(12) United States Patent
Butler

(10) Patent No.: US 7,195,743 B2
(45) Date of Patent: *Mar. 27, 2007

(54) WASTE TREATMENT

(75) Inventor: Mark Henry Butler, Barden Ridge (AU)

(73) Assignee: Medivac Technology PTY Limited, Castle Hill (AU)

(*) Notice: Subject to any disclaimer, the term of this patent is extended or adjusted under 35 U.S.C. 154(b) by 587 days.

This patent is subject to a terminal disclaimer.

(21) Appl. No.: 10/380,496

(22) PCT Filed: Oct. 10, 2001

(86) PCT No.: PCT/AU01/01296

§ 371 (c)(1),
(2), (4) Date: Mar. 14, 2003

(87) PCT Pub. No.: WO02/30476

PCT Pub. Date: Apr. 18, 2002

(65) Prior Publication Data

US 2004/0037763 A1 Feb. 26, 2004

(30) Foreign Application Priority Data

Oct. 10, 2000 (AU) .................... PR 0667

(51) Int. Cl.
*A61L 9/00* (2006.01)

(52) U.S. Cl. .............. 422/292; 422/298; 422/309; 241/606

(58) Field of Classification Search .......... 422/26, 422/292, 298, 309; 241/606

See application file for complete search history.

(56) References Cited

U.S. PATENT DOCUMENTS

| | | | | |
|---|---|---|---|---|
| 3,043,480 A | * | 7/1962 | Wittrock | 222/146.5 |
| 3,717,434 A | * | 2/1973 | Black | 422/112 |
| 4,366,928 A | * | 1/1983 | Hughes | 241/30 |
| 4,644,809 A | * | 2/1987 | Howse | 74/25 |
| 4,961,540 A | * | 10/1990 | Wiesemann | 241/46.06 |
| 4,964,914 A | * | 10/1990 | Leath | 106/745 |
| 5,035,367 A | * | 7/1991 | Nojima | 241/37.5 |
| 5,362,443 A | * | 11/1994 | Tanaka et al. | 422/26 |
| 5,364,589 A | * | 11/1994 | Buehler et al. | 422/26 |
| 5,424,033 A | * | 6/1995 | Roland | 422/26 |
| 5,614,157 A | * | 3/1997 | Hall | 422/307 |
| 6,155,964 A | * | 12/2000 | Hensley | 494/9 |
| 6,732,962 B1 | * | 5/2004 | Butler | 241/57 |

FOREIGN PATENT DOCUMENTS

| | | |
|---|---|---|
| DE | 196 27 044 A | 1/1998 |
| DE | 19627044 A1 | 1/1998 |
| JP | 401249142 A * | 10/1989 |
| WO | WO 00 38744 A | 7/2000 |
| WO | WO 00/67808 A | 11/2000 |
| WO | WO 01/43786 A | 6/2001 |

* cited by examiner

Primary Examiner—Krisanne Jastrzab
(74) Attorney, Agent, or Firm—Pearne & Gordon LLP

(57) ABSTRACT

Disclosed is a combination instrument steriliser (13, 210) and biomedical waste processor (15, 211). Both units are supplied steam from a common steam boiler (30, 212). In preferred embodiments, the waste processor utilises a shredder comprising a planetary gear box (127) with rotating cutting heads (120, 200).

10 Claims, 4 Drawing Sheets

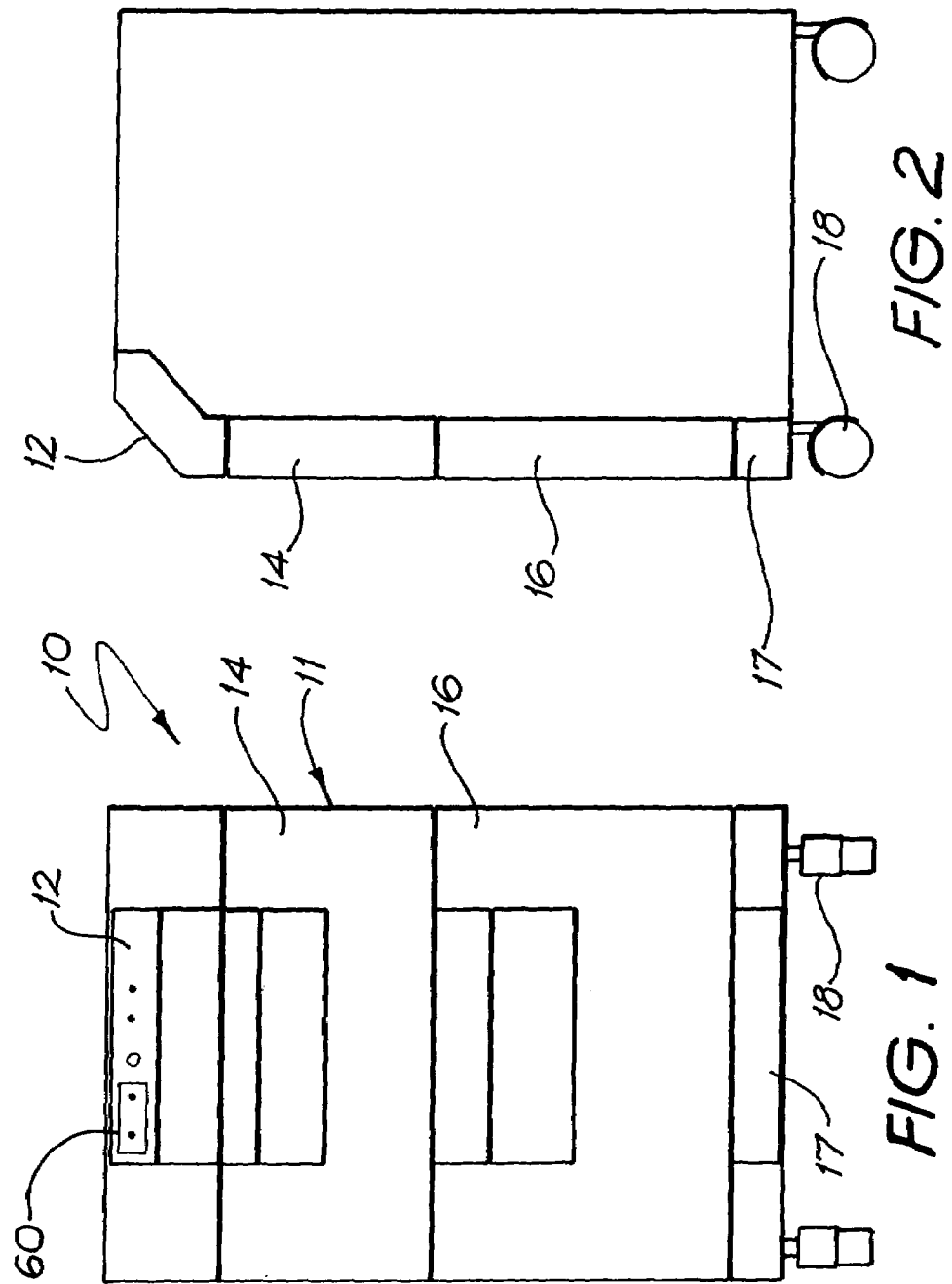

WASTE TREATMENT

FIELD OF THE INVENTION

The invention pertains to the sterilisation of biomedical waste and medical instruments and more particularly to a compact combination of biomedical waste processor and instrument steriliser.

BACKGROUND ART

Many current methods of treating medical waste are expensive, require a large amount of space and cause damage to the environment because the energy consumption of such devices is disproportionate to the size of the batches of waste being processed.

DISCLOSURE OF THE INVENTION

According to one aspect of the invention there is provided a combined waste processor and instrument steriliser device comprising:

a housing having, a first sealable compartment containing one or more trays for holding instruments and a second sealable compartment containing a waste processing device, the waste processing device including a hopper which leads to a shredder; and a boiler located within the housing for supplying steam to the first and second compartments.

According to another aspect of the invention there is provided a waste processing and instrument sterilising device, comprising:

a first separate and sealable compartment, holding one or more trays for holding instruments;

a second, separate, sealable compartment in which is located a biomedical waste processing device, the waste processing device comprising a hopper which leads to a shredder; and a third separate compartment containing a boiler for supplying steam to the first and second separate compartments.

In preferred embodiments of the invention, both the biomedical waste steriliser and instrument steriliser are supplied with steam from a common steam generator.

In other embodiments of the invention, the operation of the device is governed by a programmable logic device which supplies data to a log file of the device's activity.

In preferred embodiments of the invention the biomedical waste shredder incorporates a planetary gear box in which the planet gears drive a cluster of rotating cutters.

In particular embodiments of the invention, the cluster rotates in a first direction and the individual cutters rotate in an opposite direction.

BRIEF DESCRIPTION OF THE DRAWINGS

FIG. 1 is a front elevation of an appliance according to the teachings of the present invention;

FIG. 2 is a side elevation of the device depicted in FIG. 1;

MODES FOR CARRYING OUT THE INVENTION

Figure 3:
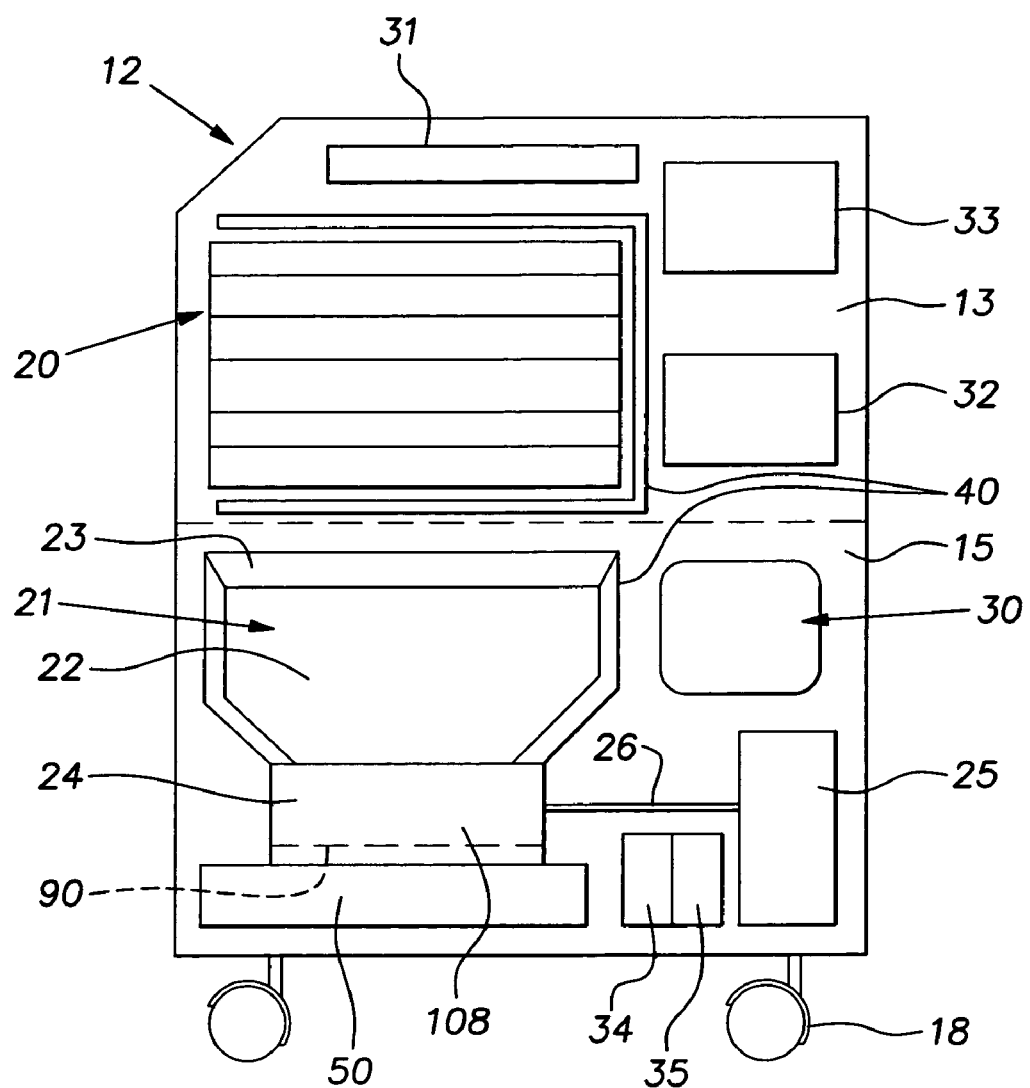
FIG. 3 is a schematic side elevation, partially cross-sectioned, of the device depicted in FIGS. 1 and 2.

As shown in FIG. 1 a combination biomedical waste processor and instrument steriliser 10 is packaged within a single housing 11. The housing 11 incorporates an instrument panel 12, a sealed upper compartment 13 which is accessed with a sliding door 14, a sealed lower compartment 15 which is accessed by a hinged door or sliding drawer 16 and a lower sliding drawer 17 which provides access to processed waste material. The control panel 12 may also incorporate a touch screen display 60. The housing 11 and working surfaces are preferably formed from stainless steel and the entire apparatus 10 may be mounted on castors or wheels 18. The device 10 is sized for under bench top use.

In preferred embodiments the door or drawer 14 provides access to an arrangement of stacked trays 20 which are adapted to receive medical instruments for sterilisation.

The lower compartment 15 contains a biomedical waste shredder and steriliser 21. The door or drawer 16 allows contaminated waste to be introduced into a hopper 22. When the door or drawer 16 is closed, a counterweight 23 urges the contents of the hopper 22 toward a shredder 24. The hopper 22, trays 20 and shredder area may be provided with a steam jacket 40 which is supplied either externally or from an internal boiler 30. The steam jacket may be used to preheat the contents of the hopper 22 prior to a during delivery to the shredder mechanism 24. The sterilised and shredded waste is delivered to a user accessible compartment 50 which is accessible through the drawer 17 on the front of the device 10.

The shredder 24 is driven by an electric motor 25 through a belt or chain drive 26.

In preferred embodiments, the steam is supplied at a pressure of 200 KpA and a temperature of 134° C. A typical program comprises the administration of pressurised steam for approximately 3.5 minutes. Depending on the hopper size the device is capable of a throughput rate of approximately 10–15 liters per cycle and may operate from a standard 10 amp/240 volt power supply. A programme logic controller 31 permits a range of user determined or pre-programmed cycles to suite the specific needs of almost any application requirement.

The device 10 may also be equipped with a vacuum pump 32 which is intended to evacuate the ambient air prior to instrument or waste steam treatment and may also be used to evacuate the device after steam treatment.

The device 10 also incorporates a high efficiency particle arrester (HEPA) 33 for the treatment of discharge gases.

Also provided is a condenser 34 and a water filter 35 for treating the gases and liquid by-products of the shredding and sterilisation process.

Figure 4:
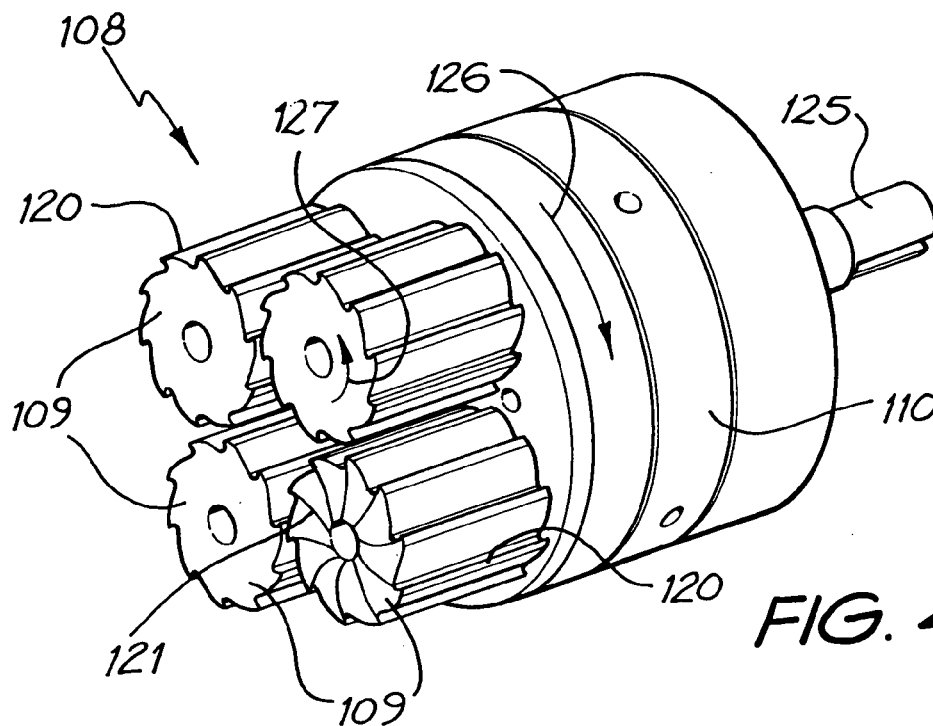
FIG. 4 is a perspective view of a shredder incorporating a planetary gear box according to the teachings of the present invention.

As shown in FIG. 4 a preferred shredding mechanism 108 comprises a planetary gear box 110 which is driven by the motor 25. The planet gears of the gearbox 108 each drive a rotating cutter 109. Each cutter features longitudinal cutting edges 120 and may also include optional radially disposed cutting edges 121 on the end faces of one or more of the cutters 109. In some preferred embodiments, the rotation of the central shaft 125 of the gear box 110 causes the cluster of cutting heads 109 to rotate in one direction 126 and the individual cutters 109 to rotate in an opposite direction 127.

Figure 5:
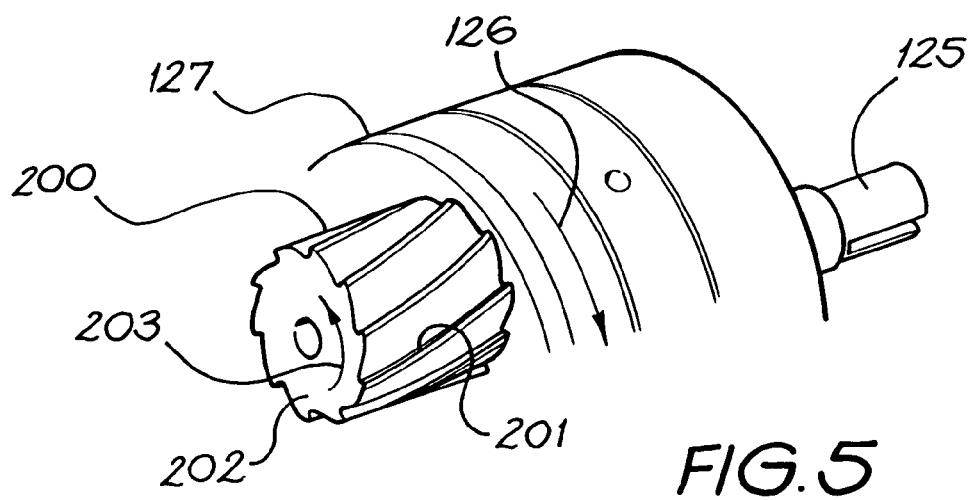
FIG. 5 is a perspective view of a planetary gear box incorporating a cutter with anti-sense helical cutting edges.

As shown in FIG. 5, the rotating cutter 200 may incorporate helical cutting edges rather than the longitudinal cutting edges 120 depicted in FIG. 4. In the example depicted at FIG. 5, the helical cutting edges 201 are provided in an anti-sense direction. Thus, waste coming in contact with the helical edges 201 are urged toward the face 202 of the cutter rather than toward the gear box 127 when the cutter is rotated in the direction of the arrow 203.

The device 10 is also capable of providing on-line system diagnostics and real time data links to other devices. It may be optionally controlled by a personal digital assistant (PDA) and can provide log files of its operation in any number of formats.

In operation, an operator loads waste into the hopper 22 and the hatch door 16 is sealed manually or automatically. Unless this is done the system will not operate. The counter weight 23 maintains a back pressure upon the waste on door closure. Then the device is started.

A vacuum is delivered to remove all air, with the outgoing air flashed on an incoming steam line and filtered through HEPA and option ozone or UV treatments.

Thereafter, the internal boiler 30, or external steam source delivers steam to the treatment chamber via multiple steam points. In the alternative, an internal heater converts waste fluids to steam and a dynamic saturated steam environment is established. A preset temperature is maintained (134° C. for 3.5 minutes) within a total 7-minute cycle.

The multiple cutters 109 rotate in one direction, grabbing and tearing the product while the drive head 110 rotates in the opposite direction transporting the material around the inside of the treatment chamber. Once the required residence time has been achieved the steam is vented down to atmospheric pressure and upon reaching the pre-specified safe condition the discharge door 17 is automatically released. The cutters continue to operate for three minutes and the waste is forced against a specially designed grating 90 where the shredded material takes the path of least resistance and extruded through the holes to the discharge chamber/bags.

The hole-size in the grating 90 effectively controls the cross-section of the discharged material.

A post treatment vacuum is delivered to remove condensate and facilitate drying of the shredded waste as the cutters continue to provide a dynamic environment.

After the treatment cycle the unit can be purged with steam to sanitise the internal surfaces of the machine.

The feed and cutter units are powered by an electric transmission 25, 26 with the automated treatment sequence controlled by a PLC 31. This feature means that the unit can operate on a standard domestic power supply.

The device has a throughput rate of 10–15 liters per cycle at 134° C. depending on the material involved and operates from a standard 10 amp/240 volt power supply. The PLC permits a range of pre-programmed alternative cycles to suit the specific needs of almost any application requirement.

The all stainless steel machine has been designed to provide optimum performance, long life, low maintenance and ease of operation.

Figure 6:
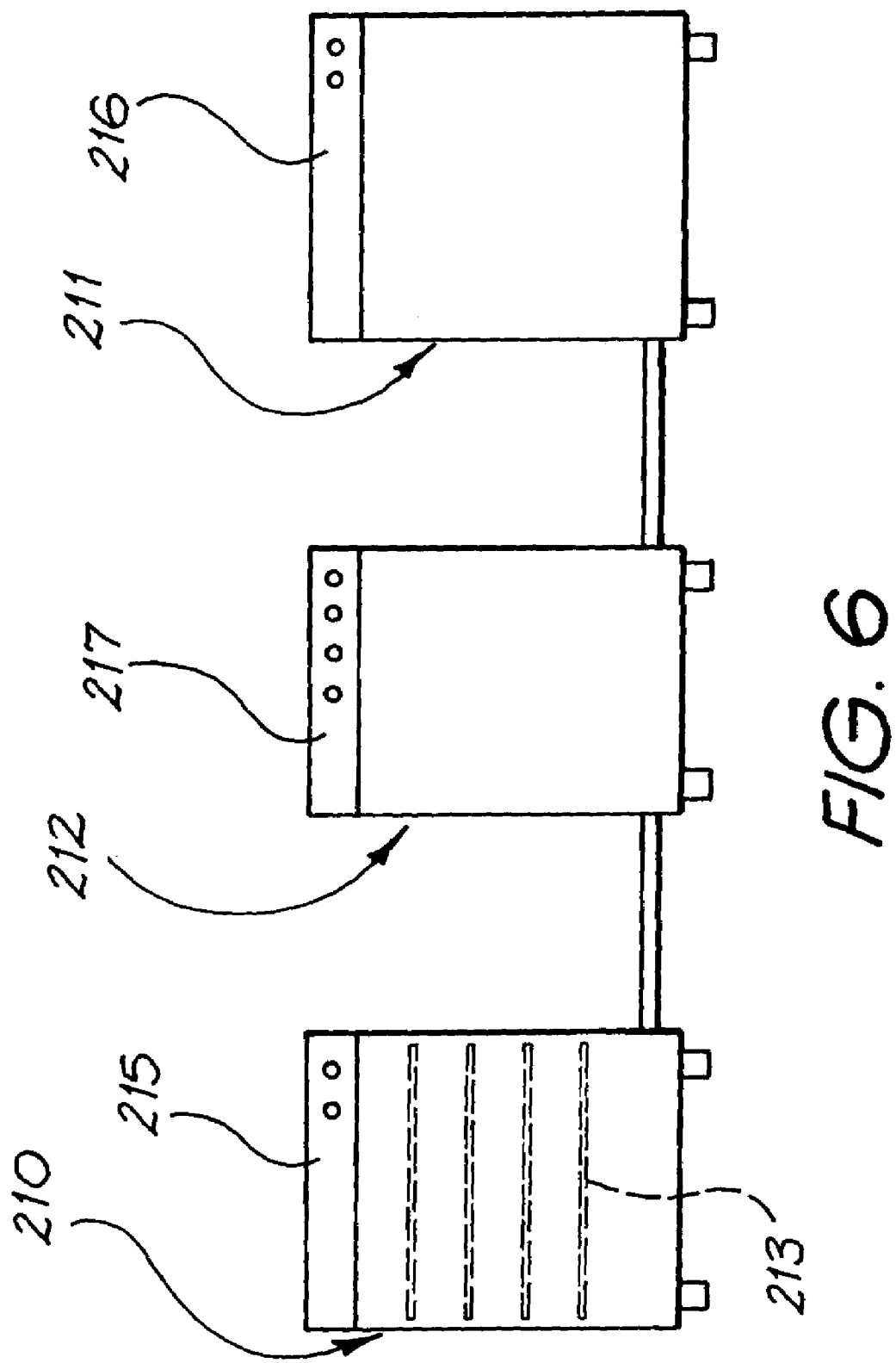
FIG. 6 is a schematic view of a device utilising a common steam boiler to supply a medical instrument steriliser and placed sterilisation unit.

As shown in FIG. 6, what were effectively the upper compartment 13 and lower compartment 15 may be provided as separate units 210, 211 which are supplied by a common steam generator or boiler 212. The separate compartment 210 contains an arrangement of stacked trays 213 which are adapted to receive medical instruments for sterilisation. The other separate compartment 211 contains a biomedical waste shredder and steriliser of the type depicted in FIG. 3. Separate instrument controls 215, 216 may be provided on each of the separate compartments 210, 211. In the alternative, a common control panel 217 may be located on the steam boiler 212 so as to control both compartments 210, 211. In this way, the instrument steriliser 210 may be physically separated from the waste sterilisation unit 211.

It will be appreciated that the utilisation of the present invention will result in considerable cost savings to institutions and individuals with respect to their disposal costs. The utilisation of the invention also allows for greater control over future costs, handling costs and transport liabilities.

While the invention has been disclosed with reference to particulars details of construction these have been provided by way of example and not as limitations to the scope or spirit of the invention.

The invention claimed is:

1. A combined waste processor and instrument sterilizer device comprising:
a housing having, a first sealable compartment containing one or more trays for holding instruments and a second sealable compartment containing a waste processing device, the waste processing device including a shredder and a hopper which leads to the shredder; and a boiler located within the housing for supplying steam to the first and second compartments, wherein the shredder comprises a planetary gear box driven by a motor to rotate in one direction, a gear box having a plurality of rotating cutters, which are rotated by the gear box in an opposite direction and wherein each cutter has helical cutting edges.

2. The device of claim 1, wherein the first compartment is located above the second compartment.

3. The device of claim 1, wherein the boiler is located within a third compartment.

4. The device of claim 1, wherein each cutting edge is an anti-sense helical cutting edge.

5. The device of claim 1, wherein the or each tray is provided with a steam jacket.

6. The device of claim 1, wherein the shredder is provided with a steam jacket.

7. The device of claim 1, wherein the waste processing device further comprises a vacuum pump for evacuating ambient air prior to a steam treatment or after it.

8. The device of claim 1, further comprising a particle arrester for the treatment of a discharged gas.

9. The device of claim 1, further comprising a grating adjacent to a cutter against which waste is forced by the cutter and through which waste passes prior to entering a discharge chamber.

10. The device of claim 1 including a programmable logic unit for supplying data to a log file of the activity of the device.

* * * * *